United States Patent
Hoke, II et al.

(10) Patent No.: US 9,314,410 B2
(45) Date of Patent: *Apr. 19, 2016

(54) ORAL CARE COMPOSITIONS COMPRISING PHYTIC ACID

(75) Inventors: Steven Hamilton Hoke, II, West Chester, OH (US); Ross Strand, Beijing (CN); Xiaoli Wang, Beijing (CN); Yiqun Zhang, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/547,186

(22) Filed: Jul. 12, 2012

(65) Prior Publication Data
US 2013/0017158 A1 Jan. 17, 2013

(30) Foreign Application Priority Data

Jul. 12, 2011 (CN) ................. PCT/CN2011/077065

(51) Int. Cl.
| | | |
|---|---|---|
| A61Q 11/00 | (2006.01) | |
| A61K 8/24 | (2006.01) | |
| A61K 8/21 | (2006.01) | |
| A61K 8/19 | (2006.01) | |
| A61K 8/27 | (2006.01) | |
| A61K 8/365 | (2006.01) | |
| A61K 8/55 | (2006.01) | |

(52) U.S. Cl.
CPC ... *A61K 8/19* (2013.01); *A61K 8/27* (2013.01); *A61K 8/365* (2013.01); *A61K 8/55* (2013.01); *A61Q 11/00* (2013.01); *A61K 2800/51* (2013.01); *A61K 2800/58* (2013.01)

(58) Field of Classification Search
USPC ................................. 424/49, 52, 57
See application file for complete search history.

(56) References Cited

U.S. PATENT DOCUMENTS

| | | | |
|---|---|---|---|
| 2,493,666 A * | 1/1950 | Gehman et al. | ................ 558/147 |
| 2007/0122359 A1 * | 5/2007 | Wang et al. | ...................... 424/52 |
| 2008/0138298 A1 * | 6/2008 | Glandorf et al. | ................ 424/52 |
| 2009/0136432 A1 * | 5/2009 | Strand et al. | ..................... 424/52 |
| 2010/0135921 A1 | 6/2010 | Hughes et al. | |
| 2011/0020247 A1 | 1/2011 | Strand | |

FOREIGN PATENT DOCUMENTS

| | | |
|---|---|---|
| EP | 2057978 A1 | 5/2009 |
| EP | 2281543 A1 | 2/2011 |
| WO | WO 2007/076001 A3 | 7/2007 |
| WO | WO 2008/005548 A2 | 1/2008 |

OTHER PUBLICATIONS

International Search Report for PCT/CN2011/077065—CM3628Z—Mar. 26, 2012.

* cited by examiner

*Primary Examiner* — Lezah Roberts
(74) *Attorney, Agent, or Firm* — Alexandra S. Anoff; Amanda T. Barry (57) ABSTRACT

An oral care composition comprising a stannous ion source and/or a zinc ion source; a phytic acid or a phytic acid salt or mixtures thereof; characterized in that the phytic acid or phytic acid salt has an average IPn of greater than 5.2. In a composition which comprises stannous, there is a decrease in soluble stannous whilst maintaining an equivalent efficacy to a composition comprising a higher level of soluble stannous and efficacy is observed for avoiding stain and astringency problems. When zinc ions are present, it has been surprisingly found that a decrease in soluble zinc can provide an equivalent antimicrobial efficacy to a composition comprising a greater level of soluble zinc.

3 Claims, 3 Drawing Sheets

A MS-IC trace for Phytic Acid with Average IPn 3.2

FIG 2B

A MS-IC trace for Phytic Acid with Average IPn 5.8

FIG 3

ORAL CARE COMPOSITIONS COMPRISING PHYTIC ACID

CROSS REFERENCE TO RELATED APPLICATION

This application claims the benefit of PCT application No. PCT/CN2011/077065 filed 12 Jul. 2011, which is incorporated herein by reference

FIELD OF THE INVENTION

The present invention relates to oral compositions comprising tin (II) ions and or zinc ions and phytic acid.

BACKGROUND OF THE INVENTION

Tin (II) (stannous) ions, provided in oral compositions by stannous fluoride and/or other stannous salts, have long been valued for the multiple benefits that they can afford, including antimicrobial effects, control of breath malodour, control of dental plaque growth and metabolism, reduced gingivitis, decreased progression to periodontal disease, reductions in dentinal hypersensitivity, and reduced coronal and root dental caries and erosion. Along with the benefits however there are some notorious problems. One of the most notable side effects of regular use of stannous comprising compositions is yellow-brown tooth staining. This stain is derived from pellicle, plaque and dietary component reactions with available stannous deposited on tooth surfaces during treatment with effective stannous containing formulations. Furthermore, formulating stannous ions stably also presents a challenge as the tin (II) ion is both prone to oxidation towards tin (IV) and to precipitate from aqueous solution as stannous hydroxide. The latter is a pH dependent phenomenon and is typically avoided by formulating at a low pH and/or by formulating in an anhydrous composition. Formulating at a low pH is not preferred when a fluoride source is utilised in the presence of a silica dental abrasive however because it increases the tendency of the fluoride to react with the silica. Formulating in aqueous compositions though is of advantage for reasons, such as cost and formulation flexibility. Another approach to stabilising stannous is to include a chelating agent in the composition as disclosed e.g., in U.S. Pat. No. 3,282,792, WO 96/17587, U.S. Pat. Nos. 5,004,597, 5,213,790 and US 2007/0025928.

Zinc ions are also advantageously included in oral compositions. Combining zinc ions with stannous ions can give a broader spectrum of anti-microbial activity but zinc ions also pose increased formulation challenges through competing with the chelating agents used to stabilise stannous. The astringency of zinc is also well known and it has been found that the degree of astringency depends upon the form in which zinc is present in the composition.

EP 426 213 discloses oral compositions comprising the combination of zinc and stannous as an anti-plaque system. WO 94/14406 and WO 94/14407 describe formulating a source of zinc ions, preferably zinc oxide or zinc nitrate, along with sources of citrate and pyrophosphate ions in defined ratios. WO 00/61092 discloses increasing the bioavailability of zinc in a dentifrice by buffering the dentifrice at a pH of from 3 to 5.5. Its zinc is provided by slightly soluble zinc compounds, especially zinc citrate.

WO 2007/076001 discloses oral care compositions comprising an essentially water-insoluble zinc compound and phytate. Some of its example compositions include stannous ions. U.S. Pat. No. 4,335,102 discloses the use of phytic acid in an oral care composition comprising stannous for caries prophylaxis. The use of phytic acid allowed an efficacious level of stannous to be maintained in addition to improving tooth enamel's resistance to acid.

EP2057978 discloses the use of chelants, including phytic acid, in a formulation which comprises stannous and additionally comprises zinc ions, a source of fluoride ions and a silica abrasive.

Despite all of the foregoing, further improvements are needed in the formulation of stannous and zinc into oral compositions, in order to deliver antimicrobial efficacy with little staining or astringency.

It is important to have an efficacious bioavailable level of stannous and zinc to provide sensitivity and antimicrobial benefits. However, high soluble levels of these actives can lead to stain and astringency problems. It has now been found that, by controlling the level of phosphorylation of phytic acid in a composition which comprises stannous and/or zinc, there is a decrease in soluble stannous/zinc whilst maintaining an equivalent efficacy to a composition comprising a higher level of soluble stannous/zinc for antimicrobial and sensitivity benefits as well as avoiding stain and astringency problems.

SUMMARY OF THE INVENTION

The present invention relates to an oral care composition comprising:
  a) a stannous ion source and/or a zinc ion source
  b) phytic acid or a phytic acid salt or mixtures thereof,
  characterised in that the phytic acid or phytic acid salt has an average IPn of greater than 5.2.

This represents a high proportion of inositol hexaphosphate (IP6).

The composition of the invention has been found to give improved stain prevention without significant taste or stability problems, compared to compositions comprising chelants other than phytic acid. Furthermore, when tin and zinc ions are present, improved antimicrobial benefits are obtained. When a high proportion of inositol hexaphosphate (IP6) is present, this can surprisingly be achieved with a lower level of soluble stannous and or zinc than previously thought. We have surprisingly shown that a high bio-available efficacy is not dependent on the soluble levels of the actives. It is known that stannous and zinc can be incompatible with other actives and have astringent properties. It is thus advantageous not to have high soluble levels of stannous and/or zinc.

DETAILED DESCRIPTION OF THE INVENTION

Unless specified otherwise, all percentages and ratios herein are by weight of the total composition and all measurements are made at 25° C.

The present invention relates to an aqueous oral composition. The composition can be in the form of a mouth spray, mouthwash or a toothpaste or gel. Preferably the composition is in the form of a toothpaste or tooth gel suitable for use in brushing teeth.

Stannous Ions

The oral composition of the present invention preferably comprises a source of stannous ions sufficient to provide from 0.1 to 2%, preferably from 0.1 to 1%, more preferably from 0.2 to 0.7% stannous (tin (II)) ions by weight of the composition. It is an advantage of the present invention that though the stannous ions are made readily bioavailable by being substantially solubilised within the composition, the starting source of stannous ions is not critical. Suitable stannous sources include stannous fluoride, stannous chloride, stannous acetate, stannous gluconate, stannous oxalate, stannous sulfate, stannous lactate and stannous tartrate. Especially preferred sources of tin (II) ions are stannous chloride, stannous fluoride, stannous gluconate and mixtures thereof. In preferred compositions of the present invention the level of soluble tin ion is in the range of from 200 to 6000 ppm, preferably from 300 to 1000 ppm (diluted 3:1).

Zinc Ions

A preferred ingredient of the oral composition herein is a source of zinc ions sufficient to provide from 0.1 to 1.5%, preferably from 0.1 to 1%, more preferably from 0.15 to 0.5% zinc ions by weight of the composition in order to provide antimicrobial benefits. When zinc ions are present, it has been surprisingly found that a decrease in soluble zinc can provide an equivalent antimicrobial efficacy to a composition comprising a greater level of soluble zinc when phytic acid with a high level of phosphorylation is utilised. It is an advantage of the present invention that the zinc ions are made readily bioavailable by being substantially solubilised within the composition. It is not necessary however that the source of zinc ions added to the composition should itself be water soluble since some chelating agents, such as citric acid, have the capacity to solubilise the zinc when the composition is prepared. Thus insoluble or sparingly soluble zinc compounds, such as zinc oxide or zinc carbonate, can be used as the zinc source. Preferred zinc sources however are soluble zinc sources such as zinc chloride or zinc sulphate. More preferred zinc sources are those where the zinc is already combined with a suitable chelating agent in the form of a salt or other complex, such as zinc citrate, zinc gluconate, zinc lactate and zinc glycinate. Especially preferred sources of zinc ions are zinc citrate, zinc gluconate, zinc lactate and mixtures thereof. In preferred compositions of the present invention the level of soluble zinc ion is in the range from 100 to 6000 ppm, preferably from 100 to 700 ppm (diluted 3:1).

Phytic Acid

The oral composition of the invention comprises a phytic acid or a phytic acid salt. Phytic acid is a chelant, also known as a chelating agent. The term "chelant", as used herein means a bi- or multidentate ligand having at least two groups capable of binding to stannous ions and preferably other divalent or polyvalent metal ions and which, at least as part of a chelant mixture, is capable of solubilising the stannous ions and other optional metal ions within the oral composition. Groups capable of binding to stannous and other metal ions include carboxyl, hydroxyl and amine groups. The average number of phosphorylated substitutions on the inositol ring can be defined as IPn, where n is the mean number of phosphate groups on inositol. Though phytic acid is often used to refer solely to inositol hexakisphosphate (IP6), commercial sources of phytic acid often comprise substantial amounts of inositol having lesser degrees of phosphorylation (IPn), such as IP2, IP3, IP4 and IP5. For example, one commercially available phytic acid has an IPn of 3.2. Other impurities, such as free orthophosphate may also be present in phytic acid solutions. The structure of inositol hexaphosphate (IP6) is given below:

The present invention comprises a source of phytic acid or a phytic acid salt or mixtures thereof wherein the phytic acid has an average IPn of greater than 5.2. This represents a high proportion of inositol hexaphosphate (IP6). Preferred phytic acid salts are sodium phytate, potassium phytate and mixtures thereof. Methodology for determining the IPn is described below.

It is thought that in order to deliver beneficial effects from tin and zinc, the stabilised species should be available, i.e soluble as measured, and they should also be bio-available, whereby the amount and rate of delivery across the tooth enamel and the oral mucosa is critical. Without wishing to be bound by theory, it is thought that there is an IPn dependence on the solubility of the metal species, where at higher metal concentrations, the higher IPn species forms a precipitate, whereas the lower IPn species stays at least partially soluble even at higher metal concentrations. The resultant metal-phytate species of the higher IPn still provide bio-available efficacy within the oral cavity, as demonstrated by several performance benefits (see particularly Examples 4 to 7).

Further Chelating Agents

The composition of the present invention may comprise a further chelating agent. Suitable chelants herein include $C_2$-$C_6$ dicarboxylic and tricarboxylic acids, such as succinic acid, malic acid, tartaric acid and citric acid; $C_3$-$C_6$ monocarboxylic acids substituted with hydroxyl, such as gluconic acid; picolinic acid; amino acids such as glycine; salts thereof and mixtures thereof. The chelant can also be a polymer or copolymer in which the chelating ligands are on the same or adjacent monomer. Preferred chelant polymers are polyacids selected from the group consisting of a homopolymer of a monomer, a copolymer of two or more different monomers, and a combination thereof wherein the monomer or at least one of the two or more different monomers is selected from the group consisting of acrylic acid, methacrylic acid, itaconic acid, maleic acid, glutaconic acid, aconitic acid, citraconic acid, mesaconic acid, fumaric acid and tiglic acid. Particularly preferred is a methylvinylether/maleic acid (PVM/MA) copolymer. Also suitable are tripolyphosphates. Longer chain linear polyphosphates, though good chelants, are susceptible to hydrolysis in aqueous compositions. Upon hydrolysis they form orthophosphates which form insoluble zinc complexes. In one embodiment the composition comprises less than 0.1% of polyphosphates having a chain length of four or more. The chelants in the composition will preferably be in range 0.1% to 10% of the composition to stabilize the stannous ions. Preferred organic acid chelants herein comprise citrate, malate, tartrate, gluconate, succinate, lactate, malonate, maleate, and mixtures thereof, whether added in their free acid or salt forms.

Fluoride Ions

A highly preferred ingredient herein is a source of fluoride ions. It is common to have a water-soluble fluoride compound present in dentifrices and other oral compositions in an amount sufficient to give a fluoride ion concentration sufficient to provide anticaries effectiveness. The oral composition herein preferably comprises a fluoride ion source sufficient to provide from 0.01% to 0.35% (100 to 3500 ppm), preferably from 0.03% to 0.2% (300 to 2000 ppm) fluoride ion. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al. Representative fluoride ion sources include: stannous fluoride, sodium fluoride, potassium fluoride, sodium monofluorophosphate, indium fluoride and many others. Preferred sources of fluoride ion are stannous fluoride and sodium fluoride, as well as mixtures thereof.

Abrasive

Dental abrasives are useful in oral compositions such as tooth pastes and gels for their ability to remove surface stain and pellicle and for polishing the teeth. A dental abrasive is a highly preferred ingredient of the present composition. Dental abrasives useful in the present oral composition of the subject invention include many different materials. The material selected must be one which is compatible with the composition of interest and does not excessively abrade dentin. Suitable abrasives include, for example, silicas including gels and precipitates, fused silica, insoluble sodium polymetaphosphate, hydrated alumina, and resinous abrasive materials such as particulate condensation products of urea and formaldehyde.

Silica dental abrasives of various types are preferred herein because of their unique benefits of exceptional dental cleaning and polishing performance without unduly abrading tooth enamel or dentine. Silica abrasive polishing materials herein, as well as other abrasives, generally have an average particle size ranging from 0.1 to 30 μm, and preferably from 5 to 15 μm. The abrasive can be precipitated silica or silica gels such as the silica xerogels described in U.S. Pat. Nos. 3,538,230 and 3,862,307. Examples include the silica xerogels marketed under the trade name "Syloid" by the W.R. Grace & Company, Davison Chemical Division and precipitated silica materials such as those marketed by the J. M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the present invention are described in more detail in U.S. Pat. Nos. 4,340,583, 5,603,920, 5,589,160, 5,658,553, 5,651,958 and 6,740,311.

Mixtures of abrasives can be used, such as mixtures of the various grades of Zeodent® silica abrasives listed above. The total amount of abrasive in dentifrice compositions of the present invention typically ranges from 6% to 50% by weight of the composition. Dental solution, mouth spray, mouthwash and non-abrasive gel compositions of the subject invention typically contain little or no abrasive.

Water

The term "orally acceptable carrier" as used means a liquid or semi-solid vehicle such as a paste or a gel for containing the active ingredients of the present invention and delivering them to the oral cavity. The carrier may include at least 20% total water. Water is commonly used as a carrier material in oral compositions. It is useful as a processing aid, is benign to the mouth and it assists in quick foaming of toothpastes. Water may be added as an ingredient in its own right or it may be present as a carrier in other common raw materials such as sorbitol and sodium lauryl sulphate. The term 'total water' as used herein means the total amount of water present in the composition, whether added separately or as a solvent or carrier for other raw materials but excluding that which may be present as water of crystallisation in certain inorganic salts. Preferred dentifrice compositions herein are aqueous compositions comprising from 20% to 65%, preferably from 30% to 55%, more preferably from 40% to 50% total water. The carrier can also include other conventional additives in oral care compositions such as desensitizing agents, teeth whitening agents such as peroxide sources, herbal agents, buffers, anti-staining agents, thickening materials, humectants, surfactants, a flavour system, sweetening agents, and colouring agents. The oral compositions herein are preferably single phase, by which is meant that all of the ingredients of the composition are containable within in a single compartment of a container and no further mixing is required before use.

The pH of the compositions herein is preferably from 4.5 to 7, more preferably from 5 to 6.5, and even more preferably from 5.5 to 6.0. The pH of a dentifrice composition is measured from a 3:1 aqueous slurry of the dentifrice, i.e., 3 parts water to 1 part dentifrice.

Other Ingredients

The present oral composition can comprise the usual and conventional ancillary components as more fully described hereinafter.

An optional but preferred component of the compositions herein is a humectant. The humectant serves to keep the dentifrice from hardening upon exposure to air, to give a moist feel to the mouth, and, for particular humectants, to impart a desirable sweetness of flavour. The humectant, on a pure humectant basis, generally comprises from 5% to 70%, preferably from 15% to 45%, by weight of the composition. Suitable humectants include edible polyhydric alcohols such as glycerin, sorbitol, xylitol, butylene glycol, polyethylene glycol, and propylene glycol, especially sorbitol and glycerin.

The compositions of the present invention will generally also include a surfactant. Useful surfactant types include anionic, nonionic, cationic and betaine surfactants. Anionic surfactants can be included to provide cleaning and foaming properties, and are typically used in an amount from 0.1% to 2.5%, preferably from 0.3% to 2.5% and most preferably from 0.5% to 2.0% by weight. Cationic surfactants can also be used though care needs to be taken over their compatibility with other ingredients. They would typically be used at levels similar to those of the additional anionic surfactants, as would betaine surfactants. Some nonionic surfactants may be useful at substantially higher levels, such as up to 20% if it is desired to use them to form a ringing gel.

Anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Also useful herein are sarcosinate surfactants, alkyl sulfoacetates, isethionate surfactants and taurate surfactants, such as lauroyl sarcosinate, myristoyl sarcosinate, palmitoyl sarcosinate, stearoyl sarcosinate and oleoyl sarcosinate. All of the foregoing are generally used as their alkali metal or ammonium salts.

Examples of suitable nonionic surfactants include the poloxamers, polyethylene oxide condensates of alkyl phenols, long chain tertiary amine oxides, long chain tertiary phosphine oxides, long chain dialkyl sulfoxides and mixtures of such materials. Preferred betaine surfactants include cocoamidoethyl betaine, cocoamidopropyl betaine, lauramidopropyl betaine and the like.

Cationic surfactants useful in the present invention include derivatives of aliphatic quaternary ammonium compounds having one long alkyl chain containing from 8 to 18 carbon atoms such as lauryl trimethylammonium chloride; cetyl pyridinium chloride; cetyl trimethylammonium bromide; di-isobutylphenoxyethyl-dimethylbenzylammonium chloride; cetyl pyridinium fluoride; etc. Some of these cationic surfactants are also useful as anti-microbial agents.

In preparing tooth pastes or gels, it is often necessary to add a thickening agent or binder to provide a desirable consistency of the composition, to provide desirable active release characteristics upon use, to provide shelf stability, and to provide stability of the composition, etc. Thickening agents can include carboxyvinyl polymers, carrageenan, nonionic cellulose derivatives such as hydroxyethyl cellulose (HEC), and water soluble salts of cellulose derivatives such as sodium carboxymethylcellulose (NaCMC). Natural gums such as gum karaya, xanthan gum, gum arabic, and gum tragacanth can also be used herein. Suitable thickening agent levels can range from 0.1 to 5%, and higher if necessary.

The present composition, when it contains stannous ions, can be used to treat dental hypersensivity, caused by uncovered dentin. Uncovered dentin makes the tubules vulnerable to a variety of stimuli which can induce pain. This is thought to be as a result of fluid movement within the dentinal tubules stimulating nerve fibres. The physical or chemical deposition of deposits into open dentinal tubuli is an accepted mechanism of action for effective treatment of hypersensitivity. Stannous salts have been shown to deposit into tubules from neat solutions and from simple formulations. Deposition may include reactivity with mineral, collagen or dentinal fluid. A key mechanism for stannous salts anti-hypersensitivity may be to actively block tubules through deposition mechanisms—either mineral or fluid.

Another optional component of the present composition is a further dentinal desensitizing agent to control hypersensitivity, especially salts of potassium and strontium such as potassium nitrate.

Organic antimicrobial agents may also be employed. Included among such agents are water insoluble non-cationic antimicrobial agents such as halogenated diphenyl ethers, particularly triclosan and essential oils such as thymol. Water soluble antimicrobials include quaternary ammonium salts such as cetyl pyridinium chloride. Enzymes are another type of active that may be used in the present compositions. Useful enzymes include those that belong to the category of proteases, lytic enzymes, plaque matrix inhibitors and oxidases. The oxidases also have whitening/cleaning activity, in addition to anti-microbial properties. Such agents are disclosed in U.S. Pat. Nos. 2,946,725, and 4,051,234.

Flavouring and sweetening agents are preferably also included in the present composition. Suitable flavouring agents and sweetening agents are well known in the art. Suitable flavour levels in the present oral compositions herein are from 0.1% to 5.0%, more preferably from 0.5% to 1.5%, by weight. Typically, a flavour oil will be manufactured in a separate step and will comprise multiple components, natural and/or synthetic in origin, in order to provide a balanced flavour which is acceptable to a broad range of people. Flavour components can be selected from mint, spice, fruit, citrus, herbal, medicinal, and common food flavour types (e.g. chocolate). Illustrative, but non-limiting examples of such components include hydrocarbons such as limonene, caryophyllene, myrcene, and humulene; alcohols such as menthol, linalool, 3-decanol, and pinocarveol; ketones such as piperitone, menthone, spicatone, and 1-carvone; aldehydes such as acetaldehyde, 3-hexanal, or n-octanal; oxides such as menthofuran, piperitone oxide, or carvyl acetate-7,7 oxide; acids such as acetic and ocenoic; and sulphides such as dimethyl sulphide. Components also include esters such as menthyl acetate, benzyl isobutyrate, and 3-octyl acetate. The flavour components may also include essential oils such as peppermint oils from e.g., Mentha piperita and Mentha arvensis; spearmint oils such as those from Mentha cardiaca and Mentha spicata; sage oil, parsley oil, marjoram oil, cassia oil, clove bud oil, cinnamon oil, orange oil, lime oil, eucalyptus oil and anise oil. Other suitable components are cinnamic aldehyde, eugenol, ionone, anethole, eucalyptol, thymol, methyl salicylate, vanillin, ethyl vanillin, and vanilla extracts. Flavour components are described in more detail in Fenaroli's Handbook of Flavor Ingredients, Third Edition, Volumes 1 & 2, CRC Press, Inc. (1995), and Steffen Arctander's Perfume and Flavour Chemicals, Volumes 1 & 2, (1969). A physiological cooling agent can also be incorporated into the flavour oil. The coolant can be any of a wide variety of materials. Included among such materials are carboxamides, menthol, acetals, ketals, diols, and mixtures thereof. Preferred coolants herein include the p-menthane carboxamide agents such as N-ethyl-p-menthane-3-carboxamide, (known commercially as "WS-3") and mixtures thereof and menthone glycerine acetal (known commercially as "MGA"). Further coolants suitable for the present invention are disclosed in WO 97/06695.

The compositions herein can further include herbal ingredients such as extracts of chamomile, oak bark, melissa, rosemary and salvia. These, and some of the herb-derived flavouring components mentioned above (such as thymol) can be included at levels just sufficient to provide a contribution to the flavour or they can be added at higher levels, such as 1% or more, in order to provide a greater therapeutic effect.

Sweetening agents which can be used include sucrose, glucose, saccharin, sucralose, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate, sucralose and sodium saccharin, and mixtures thereof. A composition preferably contains from 0.1% to 3% of these agents, more preferably from 0.1% to 1%.

The compositions may further include usual pigments, dyes and opacifiers, such as titanium dioxide. It will be appreciated that selected components for the compositions must be chemically and physically compatible with one another.

EXAMPLES

Example 1

Formulations

The following examples further describe and demonstrate toothpaste embodiments within the scope of the present invention. These examples are given solely for the purpose of illustration and are not to be construed as limitations of the present invention as many variations thereof are possible.

Toothpaste compositions according to the present invention are shown below with amounts of components in weight %. These compositions are made using conventional methods.

TABLE 1

| Ingredient | Formulations | | | | | |
|---|---|---|---|---|---|---|
| | A | B | C | D | E | F |
| Sorbitol sol. (70%) | 40.570 | 40.570 | 40.500 | 40.500 | 30.000 | 54.884 |
| Phytic acid Avg IPn 3.2 | 0.800 | — | 0.800 | 0.800 | — | — |
| Phytic acid Avg IPn 5.8 | — | 0.800 | — | — | — | — |
| Zinc Citrate | 0.533 | 0.533 | — | — | — | — |
| Zinc Lactate | — | — | 0.788 | — | — | — |
| Stannous Fluoride | — | — | — | 0.454 | — | — |
| Sodium Fluoride | 0.321 | 0.321 | 0.243 | — | 0.321 | 0.454 |
| Trisodium Orthophosphate 6- Hydrate | — | — | — | — | 0.366 | — |
| Sodium Gluconate | 1.064 | 1.064 | — | 1.064 | — | 2.082 |
| Stannous Chloride | 1.160 | 1.160 | — | — | — | 1.500 |
| Hydroxy Ethyl Cellulose | 0.300 | 0.300 | 0.300 | 0.300 | | 0.500 |
| Sodium Carboxy Methyl Cellulose | 1.300 | 1.300 | 1.300 | 1.300 | 1.100 | — |
| Carrageenan | 0.700 | 0.700 | 0.700 | 0.700 | — | 0.800 |
| Hydrated Silica Abrasive | 15.000 | 15.000 | 15.000 | 15.000 | 21.000 | 20.000 |
| Carbomer | — | — | — | — | 0.300 | — |
| Titanium Dioxide (Anatase) | 0.525 | 0.525 | 0.525 | 0.525 | 0.250 | 0.525 |
| Sodium Lautyl Sulfate (28% soln.) | 5.000 | 5.000 | 5.000 | 5.000 | 7.000 | 4.000 |
| Sodium Saccharin | 0.300 | 0.300 | 0.300 | 0.300 | 0.280 | 0.455 |
| Flavor | 1.100 | 1.100 | 1.100 | 1.000 | 0.900 | 1.000 |
| Sodium Hydroxide (50% sol.) | 1.000 | 1.000 | 1.000 | 1.000 | — | 0.800 |
| Water and minors, e.g., color soln. | qs | qs | qs | qs | qs | qs |
| Target pH | 6.0 | 6.0 | 6.0 | 5.8 | 6.4 | 4.5 |

Example 2

Calculation of IPn

Figure 1:
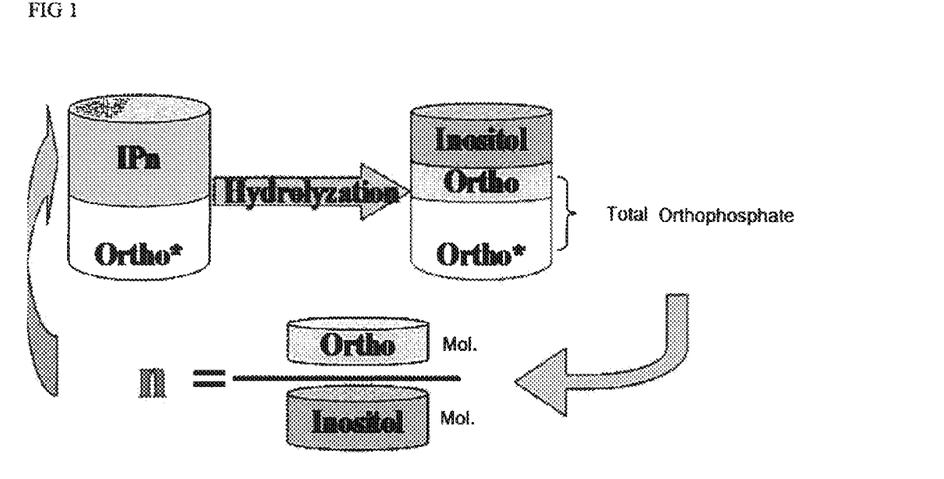
FIG. 1 shows the calculation of IPn.

Phytic acid can be hydrolyzed to inositol and phosphate. Free orthophosphate (identified as "free orthophosphate", yellow Ortho* in FIG. 1) is measured using before acid hydrolysis. Phosphate in phytic acid reacts with ammonium molybdate-ammonium metavanadate solution to deliver a yellow colour. The quantity of free orthophosphate in phytic acid is measured by testing the intensity of the yellow colour by UV-Vis spectroscopy at 420 nm. Inositol and total orthophosphate are measured after hydrolysis using standard ion chromatography techniques. The difference between total orthophosphate and free orthophosphate is the phosphate degraded from phytic acid and other phosphorylated inositols (IPx) (identified as "organic orthophosphate, the pink Ortho in FIG. 1). The molar ratio of organic phosphate and inositol represents the average substitution of phytic acid (Avg. IPn) which is calculated as follows:

$$n = \frac{(\text{Total orthophosphate \%} - \text{Free orthophosphate \%})/95}{\text{inositol \%}/180}$$

where 95 is the molecular weight of orthophosphate and 180 is the molecular weight of inositol.

Figure 2A:
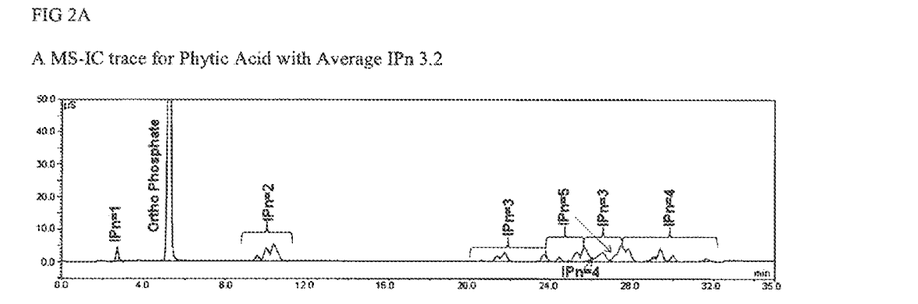
FIG. 2a shows a Mass Spectrometry-Ion Chromatography trace for phytic acid with an average IPn of 3.2.
Figure 2B:
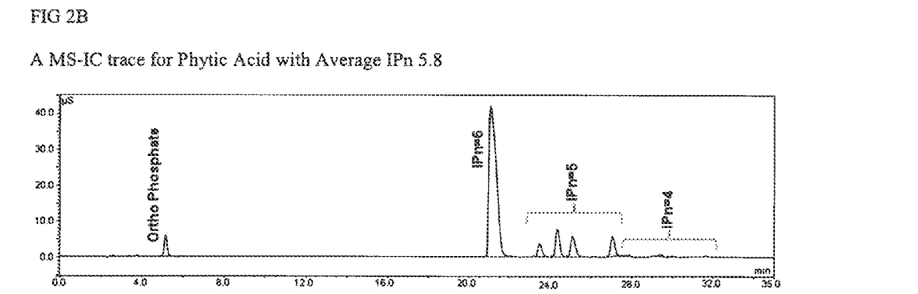
FIG. 2b shows a Mass Spectrometry-Ion Chromatography trace for phytic acid with an average IPn of 5.8.

The use of Ion Chromatography (IC)-conductivity & Mass Spectrometry (MS) analysis establishes the molecular weight for which peak is which IPn species. FIG. 2a illustrates a MS-IC trace for phytic acid with an average IPn of 3.2 and FIG. 2b illustrates a MS-IC trace for phytic acid with an average IPn of 5.8.

Example 3

Calculation of Soluble Ions

Soluble Tin
Preparation of Tin (Sn) Standard Solution, 100 µg/mL

Pipette 10 mL of the Tin stock standard solution (1000 µg/mL) into an 100 mL volumetric flask containing 30 mL of 6M HCl solution. Dilute to volume with water, cap and shake well to mix. This solution contains 100 µg/mL (ppm) Sn. Larger volumes can be prepared by making the appropriate adjustments to the reagents. The tin standard solution is stable for 1 week at room temperature.

Preparation of Blank Solution for Measurements

Add 30 mL of 6M HCl solution into an 100 mL volumetric flask. Dilute to volume with water, cap and shake well to mix. Larger volumes can be prepared by making the appropriate adjustments to the reagents.

Preparation of Sn Slurry Sample

Into a 50 ml centrifuge tube, weigh 3 g±0.01 g composition and 9 g±0.01 g deionised (DI) water. Add 6 glass balls and cap. Vortex for 2 minutes, then centrifuge for 15 mins at 15000 rpm.

Sample Solution

Weigh 2.990-3.010 grams of supernatant into a 50 mL volumetric flask and record the weight to 0.001 g.
Add 15 mL of 6M HCl and dilute to volume with DI water. Mix well.

Sample+Standard Addition 1 (20 ppm Standard Solution Spike)

Weigh 2.990-3.010 grams of supernatant into a 50 mL volumetric flask and record the weight to 0.001 g.
Pipette 10 ml of 100 ppm tin solution.
Add 15 mL of 6M HCl and dilute to volume with DI water. Mix well.

Sample+Standard Addition 2 (40 ppm Standard Solution Spike)

Weigh 2.990-3.010 grams of supernatant into a 50 mL volumetric flask and record the weight to 0.001 g.
Pipette 20 ml of 100 ppm tin solution.
Add 15 mL of 6M HCl and dilute to volume with DI water. Mix well.

Analyse the blank solution and standard addition samples for tin content using the conditions described in the instrument parameters (Table 2).

TABLE 2

| AAS settings | | |
|---|---|---|
| | Tin | Zinc |
| Wavelength | 286.3 nm | 213.9 nm |
| Flame Type | Nitrous Oxide-Acetylene | Air-Acetylene |
| Burner Head | 5 cm | 10 cm |
| Slit Width | 2.7/1.05 | 2.7/1.8 |
| Read time | 5 secs | 5 secs |
| Read delay | 3 secs | 3 secs |
| Gas flows | Nitrous oxide—6.0 L/min<br>Acetylene—7.82 L/min | Air—10.0 L/min<br>Acetylene—2.5 L/min |

Plot the absorbance versus concentration. Determine the slope, y-intercept and correlation coefficient for the standard data. It is acceptable to use the AA software to perform these calculations.

$$\text{Soluble Tin (}\mu\text{g/g in supernatant)} = \frac{X axis \text{ Intercept (}\mu\text{g/mL)} \times 50 \text{ (mL)}}{\text{Supernatant weight (g) of sample solution}}$$

Soluble Zinc
Diluted Zn Stock Standard
Pipette 1 mL of the Zinc Standard (1000 μg/mL) into the same 100 mL volumetric flask containing 30 mL of 3M HCl. Dilute to volume with water. Cap and shake well to mix. This solution contains 10 μg/mL Zn.
Calibration Standards
Pipette aliquots of the diluted Zn stock standard (10 μg/mL) into separate 100 mL volumetric flasks, as listed in Table 3 below to prepare the calibration standards for analysis of Zn. Add, as described, HCl and dilute to volume with water. Cap and shake well to mix.
All standard solutions should be prepared fresh.

TABLE 3

| Calibration Standards | | | |
|---|---|---|---|
| | Aliquot<br>Volume of Zn<br>10 μg/mL Stock<br>Standard (mL) | Aliquot<br>volume of<br>3M HCl (mL) | Volumetric<br>flask (mL) | Calibration<br>Standard<br>Concentra-<br>tion Zn<br>(μg/mL) |
| Blank | 0.0 | 30 | 100 | — |
| Std 1 | 1.0 | 30 | 100 | 0.10 |
| Std 2 | 2.0 | 30 | 100 | 0.20 |
| Std 3 | 3.0 | 30 | 100 | 0.30 |
| Std 4 | 4.0 | 30 | 100 | 0.40 |
| Std 5 | 5.0 | 30 | 100 | 0.50 |
| Std 6 | 6.0 | 30 | 100 | 0.60 |
| Check<br>Std | 3.0 | 30 | 100 | 0.30 |

Preparation of Zn Slurry Sample
Into a 50 ml centrifuge tube, weigh 3 g±0.01 g composition and 9 g±0.01 g 10% deionised water. Add 6 glass balls and cap. Vortex for 2 minutes, then centrifuge for 15 mins at 15000 rpm.
Preparation of Zn Supernatant Sample
For Products with ~300 μg/g Soluble Zinc (Preparation 1)
Weigh 1 gram of supernatant into a 250 mL volumetric flask and record the weight to 0.0001 g. Add 75 mL 3M HCl and dilute to volume with water. Take a 5 mL aliquot of this solution and add it to a 20 mL volumetric flask containing 6 mL of 3M HCl. Dilute to volume with DI water. Mix well.

For Products with ~600 μg/g Soluble Zinc (Preparation 2)
Weigh 1 gram of supernatant into a 250 ml volumetric flask and record the weight to 0.0001 g. Add 75 ml 3M HCl and dilute to volume with water. Take 5 ml aliquot of this solution and add it to a 50 ml volumetric flask containing 15 ml of 3M HCl. Dilute to volume with DI water. Mix well.
Analyse the sample solutions and standard calibration samples for zinc content using the conditions described in the instrument parameters (Table 2 AAS Settings).
Plot the absorbance versus concentration. Determine the slope, y-intercept and correlation coefficient for the standard data. It is acceptable to use the AA software to perform these calculations.
For Products Analysed Using Sample PREPARATION 1

$$\text{Soluble Zinc }\mu\text{g/g in supernatant} = \frac{\text{Zn reading from } AA \text{ (}\mu\text{g/mL)} \times 250 \text{ (mL)} \times 20 \text{ (mL)}}{\text{Supernatant weight (g)} \times 5 \text{ (mL)}}$$

For Product Analysed Using Sample PREPARATION 2

$$\text{Soluble Zinc }\mu\text{g/g in supernatant} = \frac{\text{Zn reading from } AA \text{ (}\mu\text{g/mL)} \times 250 \text{ (mL)} \times 50 \text{ (mL)}}{\text{Supernatant weight (g)} \times 5 \text{ (mL)}}$$

Soluble Fluoride
Soluble fluoride within oral compositions of the present invention and/or examples can be measured as follows.
Into a 50 ml centrifuge tube, weigh 1 g±0.01 g composition and 9 g±0.01 g deionised water. Add 6 glass balls and cap. Vortex for 2 minutes, then centrifuge for 10 mins at 15000 rpm at 37° C. Weigh 2 g±0.01 g supernatant into a beaker, add 18 g±0.01 g EDTA/TRIS buffer. Stir well to mix.
Reference solutions are made as followed.
Fluoride Stock Solution 500 mg/L F$^-$
Weigh 1.105 g+/−0.001 g sodium fluoride into a 1 L volumetric flask. Dissolve in deionised water and dilute to volume.
Weigh the amounts of EDTA and TRIS shown in Table 4 into a bottle with the specified water and dissolve.

TABLE 4

| EDTA and TRIS | | | | |
|---|---|---|---|---|
| Volume<br>water (ml) | Weight<br>EDTA (g) | Weight<br>TRIS (g) | Volume<br>Triton (ml) | Volumetric<br>Flask (L) |
| 1750 | 148.90 | 48.46 | 10 | 2 |

Adjust the pH to 8.0+/−0.05 with 50% sodium hydroxide and transfer to appropriate flask and dilute to volume. Add Triton X-100 then decant back to bottle for storage. The solution is stable for 12 months.
5 mg/L Fluoride Solution
Weigh 1 g+/−0.05 g stock solution into 10 ml plastic bottle, add 9 g+/−0.1 g deionised water, then 90 g+/−0.1 g EDTA/TRIS buffer. Cap and mix well.
25 mg/L Fluoride Solution
Weigh 5 g+/−0.05 g stock solution into 10 ml plastic bottle, add 5 g+/−0.1 g deionised water, then 90 g+/−0.1 g EDTA/TRIS buffer. Cap and mix well.

50 mg/L Fluoride Solution

Weigh 10 g+/−0.1 g stock solution into 10 ml plastic bottle, then add 90 g+/−0.1 g EDTA/TRIS buffer. Cap and mix well.

Using the above reference solutions of 5.0, 25.0 and 50.0 mg/L solutions of fluoride in EDTA/TRIS buffer the amount of fluoride can be measured using any suitable ion meter and ion selective electrode. The soluble fluoride level is calculated from the electrode reading, taking into account the dilution factor of both the sample and the references. The method can be adjusted accordingly for other fluoride salts.

Example 4

Soluble Ion Levels in Formulations with Different Average IPn

TABLE 5

Formulating with differing Avg IPn as per formulations A & B

|  | Sol. Tin (ppm diluted 3:1) | Sol Zinc (ppm diluted 3:1) | Sol Fluoride (ppm diluted 3:1) |
|---|---|---|---|
| Formula A (Avg IPn 3.2) | 550 (as made) 336 (aged 24 months) | 300 (as made) 242 (aged 24 months) | 300 (as made) 244 (aged 24 months) |
| Formula B (Avg IPn 5.8) | 410 (as made) 238 (aged 24 months) | 144 (as made) 164 (aged 24 months) | 353 (as made) 278 (aged 24 months) |

Example 5

In vitro Plaque Glycolysis and Regrowth Model

Antimicrobial efficacy can be defined in terms of a noticeable and significant reduction in in situ plaque metabolism as measured using the in vitro Plaque Glycolysis and Regrowth Model (i-PGRM).

The i-PGRM is a technique where plaque is grown from human saliva, and treated with agents designed to produce various levels of antimicrobial activity. The purpose of this technique is to provide a simple and quick method for determining if compounds have a direct effect on the metabolic pathways that plaque microorganisms utilize for the production of toxins which adversely affect gingival health. In particular, the model focuses on the production of organic acids including lactic, acetic, propionic, and butyric. This method utilizes plaque grown on polished glass rods which have been dipped in saliva overnight, soy broth and sucrose for 6 hours, and saliva again overnight. The plaque mass grown on the glass rods is then treated for 1 minute with a 3:1 water to dentifrice slurry. The mass is then placed in a soy broth/sucrose solution for 6 hours and the pH of the incubation solution is measured at the end of the 6 hours. Thus, there are measures of pre-incubation pH and post incubation pH for both test formulations and controls. This testing is typically done with a number of replicates to minimize experimental variances, and a mean pH is calculated from the replicates. Due to strong reactivity with saccharolytic organisms, compositions containing high levels of bioavailable stannous or zinc ions produce significant inhibition of plaque acid generation in the i-PGRM assay. This enables formulation variations to be compared for stability and bioavailability of stannous and zinc ions with relative ease.

The i-PGRM score is calculated according to the formula:

$$i\text{-}PGRM\ Score = 100\% \times \frac{(\text{Test product mean pH} - \text{Non-Zinc or stannous Control mean pH})}{(\text{Positive Control mean pH} - \text{Non-Zinc or stannous Control mean pH})}$$

The mean pH values refer to incubation media pH's obtained following treatment and sucrose challenge. The negative or non-Zinc control plaque samples produce large amounts of acid, and hence their pH's are lower than that of plaque samples treated with the positive control. The pH difference between the positive and negative controls would typically be a minimum of about 0.6 pH unit, ideally at least about 1.0 pH unit. The negative control (non stannous and zinc) shown as comparative example E and the positive control (high stannous) shown as comparative example F above. Such high stannous compositions have been shown to produce significant inhibition of plaque acid generation in the i-PGRM assay.

TABLE 6

Results of i-PGRM Assay of Formulations

| Formulation | i-PGRM Score % plaque inhibition vs. Negative Control |
|---|---|
| Negative Control Non-Stannous & Zinc (Example E) | 0 |
| Positive Control High Stannous (Example F) | 100 |
| IPn Average 3.2 (Example A) | 81 |
| IPn Average 5.8 (Example B) | 93 |

As shown in the results of i-PGRM assay in the table above, formulations A, B and F are effective in inhibiting plaque acid formation. Formulas A and B are statistically better at plaque inhibition vs the negative control, and Formula B has no significant difference vs. the positive control.

Example 6

Tubule Brushing Model for Sensitivity

Figure 3:
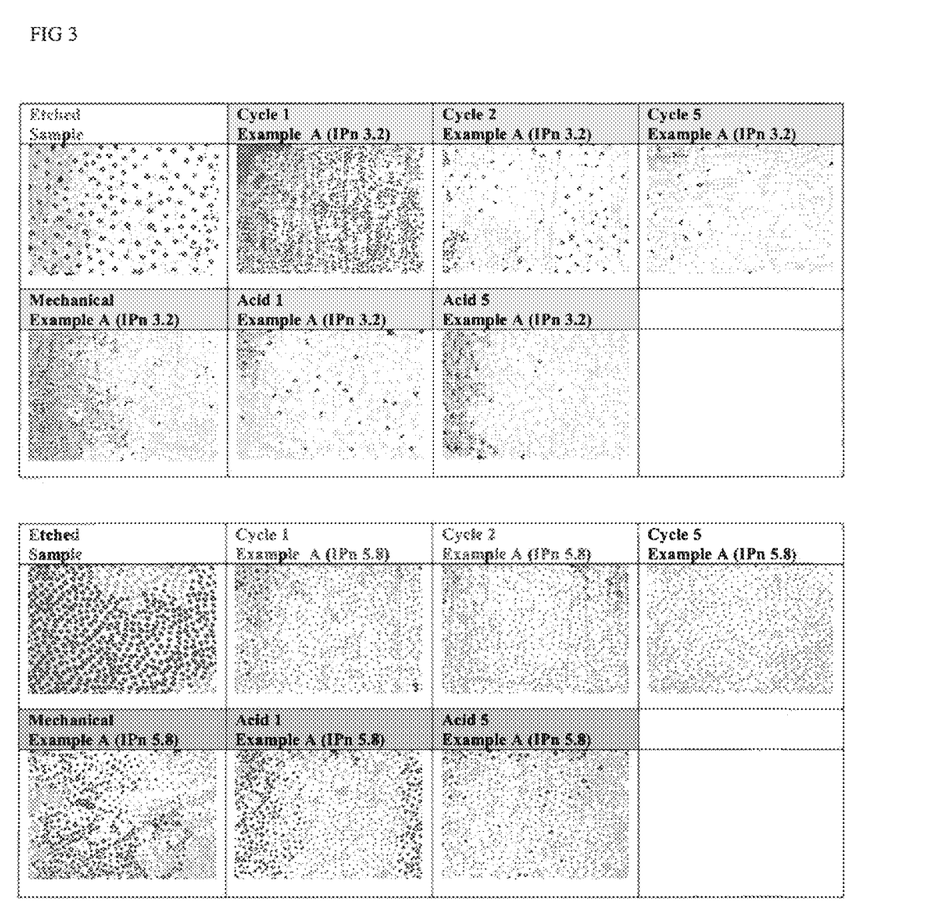
FIG. 3 shows the results of the Tubule Brushing Model for Sensitivity

Coronal-dentin specimens from intact $3^{rd}$ molars were prepared by removing the enamel layer with a precision saw and cutting a 1-2 mm section. This was then sanded with 20 μm and 9 μm lapping paper. Specimen were sonicated for one minute, to remove any extraneous matter from the surface, then etched in 6% citric acid solution for two minutes, and finally soaked in saliva to aid in pellicle formation. After imaging under the light microscopy (400×), dentin specimen were stratified and randomized into treatment groups of n=2 per treatment leg. Specimens were immersed in fresh saliva for at least 1 hr to form a pellicle prior to treatment. Each specimen was then brushed with a manual brush (ADA soft flat toothbrush) with treatment for two minutes rotating the tooth 90 degrees every 30 seconds and reapplying paste every 60 seconds. This cycle was repeated four more times for a total of 10 minutes brushing. Specimens were imaged after the first, second, and fifth cycle. After each imaging, specimens were rehydrated in deionised water overnight before further brushing. Next they were tumbled in saliva on a rotary wheel at 19 rpm for 16 hours and then imaged. Finally they were treated with acid. During the acid treatment, specimen were placed in 15 ml of regular Coca Cola® (pH 3.0) for one minute, rinsed with distilled water, and imaged. After imaging specimen were rehydrated overnight in deionised water. This acid treatment/imaging/rehydration cycle was repeated one more time for four minutes, for a total exposure to dietary acid of 5 minutes. The results are shown in FIG. 3.

Following paste treatments during cycles 1 to 5 both Formula A and Formula B show occlusion of the dentin tubules vs. the untreated etched sample control. Additionally, following the mechanical cycle challenge and the acid cycle challenge a smear layer formed which occludes the dentin tubules and has good stability and resistance.

Example 7

In-Vitro Pellicle Tea Stain Model (iPTSM)

The in vitro pellicle tea stain model (iPTSM) is a technique where an in vitro plaque biomass is grown on glass rods from pooled human stimulated saliva over the course of three days. The plaque biomass is treated with agents to determine potential dental staining levels of the various agents. The purpose of this technique is to provide a simple and quick method for determining if compounds have a direct effect on the amount of dental plaque stain. This method utilizes plaque grown on polished glass rods from pooled human saliva with treatments of 5 minutes duration, followed by a 10 minute tea treatment.
1. Roughening Glass Rods
   Polish new glass rods (5 mm×90 mm) approximately 25 mm from the untapered end on a lathe with silicon carbide paper of 240, 320, 400, and 600 grit used sequentially. After the initial polishing, polish the rods with 600 grit paper only before each test.
2. Saliva Collection & Preparation
   Collect saliva daily from a panel of 5-10 people by paraffin stimulation and refrigerate at 4° C. till needed. Pool saliva carefully (so not to pour in wax/mucus) and mix thoroughly.
3. Day 1
   Clean glass rods by sonicating with dilute HCl acid, rinse, dry, and polish with 600 grit silicon carbide paper. Rinse rods again with deionised water and dry. Insert rods into holders, adjust depth with the depth gauge on the treatment rack, and secure rods in place with rubber O-rings.
   In the early afternoon, pipette 7 ml of saliva, to which 0.1% sucrose has been added, into 16×75 mm test tubes in a dipping rack. Sucrose is added to saliva on the first day only. Place the rod holders in a modified 37° C. incubator designed to dip roughened glass rods into test tubes to a depth of 1.5 cm at 1 rpm. Dip rods overnight. The design of the incubator is fully shown in Attachment 1. Prepare plaque growth media described above and autoclave for Day 2 (saliva is added on Day 2 before use).
4. Day 2
   In the morning, add saliva to plaque growth media and mix thoroughly. Pipette 7 ml of plaque growth media into new 16/75 mm test tubes in new dipping rack. Remove old rack of used tubes, place new dipping rack into incubator, and dip rods for a minimum of six hours before replacing rods into fresh saliva for overnight dipping.
5. Day 3
   On the morning of the third day, pipette 10 ml of deionised water into 17×100 mm test tubes in the second and third rows of the treatment rack. This applies to dentifrice treatments only. Rinse solutions may or may not have water rinse tubes in the treatment rack. Pipette fresh pooled saliva into a dipping rack and set aside. Begin tea preparation by adding 550 ml to a glass beaker and heating it in the microwave for 10 minutes. At the end of ten minutes, carefully remove beaker from microwave and drop in a magnetic stir bar to dissipate the possible presence of a super-heated water core. Place 5 Lipton tea bags and a Celsius thermometer into the water and stir on a hot plate. This solution needs to be monitored to insure that it will be no hotter than 50° C. when tea treatment begins. While tea treatment is heated and mixed, prepare dentifrice slurries (1 part dentifrice to 3 parts water, also called a 1 in 4 dilution) using a handheld homogenizer for 30 seconds. Centrifuge slurries for 15 minutes at 10000 rpm. Rinse or active solutions are treated neet. Pipette 7 ml of 50° C. tea solution into a separate dipping rack. Add 5 ml of supernatant/rinse to 16×75 mm glass test tubes in the first row of the treatment rack. Turn off incubator dipping mechanics and remove old saliva dipping rack. Remove all rod holders from the incubator and place submerge rods into old saliva dipping rack to prevent drying out. Using one rod holder at a time, treat by soaking for 5 minutes in the treatment rack. If applicable, wash rods with 2×10 sec dipping in the test tubes containing the deionised water in the treatment rack. Place rod holders into prepared tea solution dipping rack and soak for 10 min. Repeat this process with all four rod holders, returning holders to dipping rack to prevent drying out. Place fresh saliva dipping rack into incubator. Return rods to the incubator after treatment/tea soak and dip in fresh saliva for at MINIMUM of 1 hour. This treatment cycle is repeated two more times with fresh treatment/tea/saliva solutions for a total of 3 treatments in a day. After the last treatment, return rods to the incubator and dip overnight in fresh saliva.
6. Day 4
   On the morning of the fourth day, turn off incubator dipping mechanics and remove rods from the saliva. Allow rods to dry are then weigh to the nearest 0.1 mg. Record weight and calculate mean dry plaque biomass weights and standard deviations. Place rods into clean sterile capable test tubes containing 3 ml of 0.5M KOH, cap tightly and digest overnight at 37° C.
6. Day 5
   On the fifth day, remove rods from the incubator and allow cooling. Vortex glass rods to insure all deposits are homogenized. Remove rods from test tubes, filter the solution through 0.45 μm cellulose acetate syringe filters and read absorbance values for each rod at 380 nm in spectrophotometer. Record results and use absorbance values to calculate mean absorbance value per treatment, standard deviations per treatment, mean absorbance per mg plaque, Standard deviations of mean absorbance per mg plaque, and % increase in absorbance per mg plaque vs. control.
7. Controls
   Usual controls for a dentifrice iPTSM run are 1 in 4 supernatants of Negative control (Formula E) and Positive control (Formula F).

TABLE 7

Results of i-PSTM Assay of Formulations

| Formulation | i-PSTM Score % Absorbance vs. Negative control |
|---|---|
| Negative Control Non-Stannous & Zinc (Example E) | 0 |
| Positive Control High Stannous (Example F) | 70.94 |
| IPn Average 3.2 (Example A) | 29.17 |
| IPn Average 5.8 (Example B) | 27.17 |

Formula A and Formula B show significantly improved stain control vs. the positive control.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition consisting essentially of:
   a) a mixture consisting of a water-soluble stannous ion source and a water-soluble zinc ion source;
   b) a chelant mixture consisting of phytic acid or a phytic acid salt or mixtures thereof and methylvinylether/maleicacid chelant copolymer as a further chelating agent;
   wherein the phytic acid or phytic acid salt has an average mean number of phosphate groups on inositol (IPn) of greater than 5.7;
   c) silica dental abrasive; and
   wherein the level of soluble stannous ion in a 3:1 diluted slurry or solution is in the range of from about 300 to about 1000 ppm; and
   wherein the level of soluble zinc ion in a 3:1 diluted slurry or solution is in the range from about 100 to about 700 ppm.

2. An oral care composition according to claim 1, further comprising a source of fluoride ions.

3. A composition according to claim 2 wherein said level of zinc ions is from about 100 to about 700 ppm and the level of stannous ions is from about 300 to about 1000 ppm and the pH of the composition is about 5 to about 6.5.

\* \* \* \* \*